United States Patent [19]

Yoshino et al.

[11] Patent Number: 4,770,997
[45] Date of Patent: Sep. 13, 1988

[54] THERMOSTABLE BILIRUBIN OXIDASE AND PRODUCTION PROCESS THEREOF

[75] Inventors: Eiichi Yoshino, Mishima; Shigeyuki Imamura, Shizuoka; Kazuo Matsuura, Shizuoka; Hideo Misaki, Shizuoka, all of Japan

[73] Assignee: Toyo Jozo Co., Ltd., Shizuoka, Japan

[21] Appl. No.: 820,011

[22] Filed: Jan. 21, 1986

[30] Foreign Application Priority Data

Feb. 5, 1985 [JP] Japan .................................. 60-20625

[51] Int. Cl.⁴ ......................... C12Q 1/26; C12N 9/02; C12R 1/10
[52] U.S. Cl. ...................................... 435/25; 435/189; 435/836
[58] Field of Search .................. 435/189, 191, 836, 25

[56] References Cited

U.S. PATENT DOCUMENTS 4,677,062 6/1987 Uwajima et al. ..................... 435/68

OTHER PUBLICATIONS

Chemical Abstracts, vol. 99, No. 3, 18 Juillet 1983, p. 337 resume No. 19274th, Columbus, Ohio, US; & JP-A-58 61 000 (Nippon Shoji Co., Ltd) 11-04-1983.

Primary Examiner—Lionel M. Shapiro
Attorney, Agent, or Firm—Oblon, Fisher, Spivak, McClelland & Maier

[57] ABSTRACT

Thermostable bilirubin oxidase having substrate specificity to at least bilirubin and capable of catalyzing a reaction in which biliverdin and water are formed from bilirubin and oxygen. It can be produced by culturing a bilirubin oxidase producing micro-organism belonging to the genus Bacillus, for example, *Bacillus licheniformis* and then preparing the resultant bilirubin oxidase from the cultured broth.

9 Claims, 2 Drawing Sheets

THERMOSTABLE BILIRUBIN OXIDASE AND PRODUCTION PROCESS THEREOF

BACKGROUND OF THE INVENTION

1. Field of the Invention

This invention relates to a novel bilirubin oxidase and to a process for its production. More specifically, this invention relates to novel thermostable bilirubin oxidase and a process for the production of bilirubin oxidase which comprises culturing a bilirubin oxidase producing microorganism belonging to the genus Bacillus and then preparing the resultant bilirubin oxidase from the cultured broth.

2. Discussion of the Background

Bilirubin oxidase has conventionally been known as an enzyme which has substrate specificity to bilirubin and catalyzes a reaction in which biliverdin and water are formed from bilirubin and oxygen. As microorganisms capable of producing bilirubin oxidase, have been reported certain Myrothecium genus [N. Tanaka and S. Murao, Agric. Biol. Chem., 46, 2499 (1982)], Schizophyllum genus (Japanese Patent Laid-Open No. 135886/1984), and Coprinus, Trametes, Lenzites, Coriolus, Pholiota, Pleurotus and Fomitopsis genus (Japanese Patent Laid-Open No. 198971/1984).

Bilirubin oxidase has been attracting interests in recent years as a reagent for determining of bilirubin content and removing bilirubin which causes errors to analysis of other biochemical substance(s) in serum samples in the field of clinical chemistry. Among conventional bilirubin oxidase samples, the Myrothecium-originated enzyme is stable for 15 minutes as 37° C. but its residual activity is as little as 20% or so at 70° C. On the other hand, the Schizophyllum-originated enzyme is stable for 10 minutes up to 45° C. only. The enzyme samples originated from other producing microorganisms, for example, the Coprinus-originated enzyme exhibits residual activity of 90-95% after held for 10 minutes at 60° C. and is not satisfactory in thermal stability. They thus require strict temperature control during their production and treatments. When they are immobilized as one way of their application, they may be deactivated depending on conditions for their immobilization. They are hence not fully satisfactory in their handling readiness.

SUMMARY OF THE INVENTION

The present inventors have proceeded with a variety of investigations. As a result, it has been found that a microorganism strain, B-0891 strain, isolated from the soil of Owakidani, Hakone-machi,, Ashigarashimo-gun, Kanagawa-ken, Japan and belonging to the genus Bacillus produces bilirubin oxidase capable of catalyzing a reaction in which biliverdin and water are formed from bilirubin and oxygen, and the thus-produced bilirubin oxidase is stable around 70° C.

The present invention has been completed based on the above finding, and relates to bilirubin oxidase which have thermostable property and substrate specificity to at least bilirubin and catalyze a reaction in which biliverdin and water are formed from bilirubin and oxygen, and to a process for producing bilirubin oxidase, which comprises culturing a bilirubin oxidase producing microorganism belonging to the genus Bacillus and then preparing the resultant bilirubin oxidase from the cultured broth.

The bilirubin oxidase of this invention is excellent in thermostability and hence has very little danger of inactivation or the like upon its immobilization as one way of its enzymatic application or during its handling as a clinical diagnostic. It is therefore easy to handle. The present invention has provided this novel and good bilirubin oxidase.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 2:
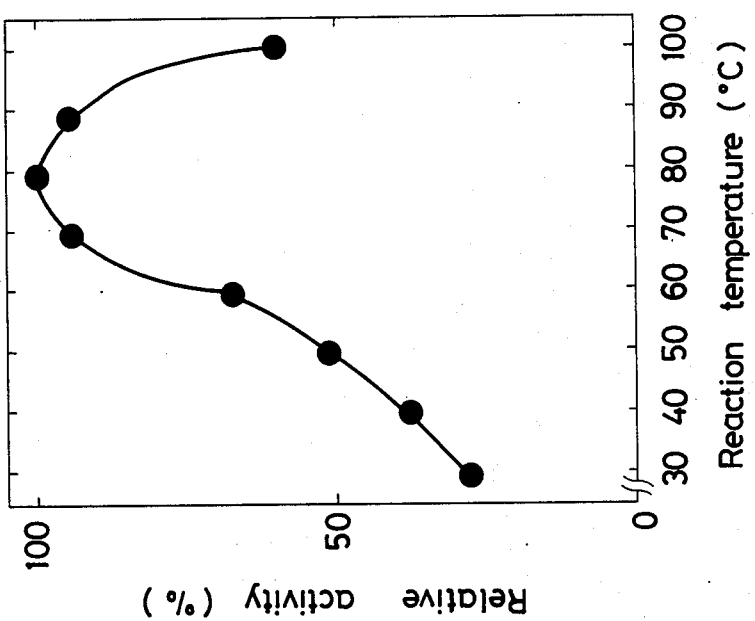
FIG. 2 illustrates the optimum temperature of the bilirubin oxidase of this invention.

The followings are certain taxonomic features of the novel bilirubin oxidase producing microorganism of this invention:

(I) Morphological features (as a result obtained after culturing at 30° C. for 24 hours on a usual agar culture):

(1) Shape, size and pleomorphism of cells:

A discrete or short-chain bacillus having round edges. Size: $0.5-0.8 \times 2.0-40$ μm. No pleomorphism.

(2) Mobility and flagella: None.

(3) Spore (shape, size, location, swelling of microorganism body): An oval or cylindrical spore of $0.5 \times 1.0$ μm is formed centrally or at a location close to the center. The microorganism body is not swollen by the spore.

(4) Gram stain: Positive.

(5) Acid-fast stain: Negative.

(II) Growth tests:

(1) Nutrient agar plate culture (28°-30° C., 24 hrs.): A circular, flat and soft colony is formed. The periphery is irregular and the surface is somewhat dry. The color is gray white and no soluble dyestuff is produced.

(2) Nutrient agar slant culture (28°-30° C., 24 hrs.): The microorganism grows in lines and shows good growth. The color is gray white and no soluble dyestuff is produced.

(3) Liquid culture (peptone solution, 28°-30° C., 24 hrs.): The growth is weak and a soft-hairy precipitate is developed.

(4) BCP milk (28°-30° C., 24 hrs.): The solution is rendered alkaline and is peptionized.

| (III) Physiological properties: | | |
|---|---|---|
| (1) | Reduction of nitric acid salts | + |
| (2) | Denitrification | − |
| (3) | MR test | − |
| (4) | VP test | + |
| (5) | Formation of hydrogen sulfide | − |
| (6) | Formation of indole | − |
| (7) | Hydrolysis of starch | + |
| (8) | Metabolization of citric acid salts | + |

-continued

| | (III) Physiological properties: | |
|---|---|---|
| | (Simmonds' medium) | |
| | Metabolization of citric acid salts | + |
| | (Christensen's medium) | |
| (9) | Metabolization of maleic acid salts | + |
| (10) | Metabolization of propionic acid salts | − |
| (11) | Formation of soluble dyestuff | − |
| (12) | Production of urease (SSR) | − |
| | Production of urease (Christensen) | − |
| (13) | Production of oxidase | + |
| (14) | Production of lecithinase | − |
| (15) | Production of catalase | + |
| (16) | Growth range (pH) | 5.0–9.0 |
| (17) | Growth temperature | |
| | 50° C. | + |
| | 20° C. | + |
| | 15° C. | − |
| (18) | Growth under anaerobic conditions | + |
| (19) | OF test | F |
| (20) | Hydrolysis of gelatin | + |
| (21) | Hydrolysis of casein | + |
| (22) | Hydrolysis of aesculin | + |
| (23) | Hydrolysis of cellulose | − |
| (24) | Hydrolysis of tyrosine | − |
| (25) | Salt resistance | up to 4% |
| (26) | Growth on Sabourand's medium | + |
| (27) | GC % (Tm method) | 44% |

(IV) Production of acids and/or gas from sugars (base culture meidum: peptone-free culture medium, $NH_4H_2PO_4$ 1.0 g, KCl 0.2 g, $MgSO_4.7H_2O$ 0.2 g, yeast extract 1.0 g, agar 3.0 g, BTB (0.2%) 10.0 ml, distilled water 1000 ml, pH 7.2):

TABLE 1

| Sugar | Acid | Gas | Sugar | Acid | Gas |
|---|---|---|---|---|---|
| Adonitol | − | − | D-Mannitol | + | − |
| L-Arabinose | + | − | D-Mannose | + | − |
| Cellobiose | + | − | Melezitose | − | − |
| Dulcitol | − | − | Melibiose | − | − |
| meso-Erythritol | − | − | Raffinose | − | − |
| D-Fructose | + | − | D-Rhamnose | − | − |
| Fucose | − | − | D-Ribose | + | − |
| D-Galactose | (+) | − | Salicin | − | − |
| D-Glucose | + | − | L-Sorbose | − | − |
| Glycerin | + | − | Sorbitol | − | − |
| Inositol | + | − | Starch | + | − |
| Inulin | + | − | Sucrose | + | − |
| Lactose | − | − | Trehalose | + | − |
| Maltose | + | − | D-Xylose | + | − |

From the above-described principal characteristics, the strain of the present invention is a discrete or short-chain, round-edges, gram-positive and non-mobile bacillus microorganism. It is catalase-positive and oxidase-positive and produces acids fermentatively from glucose. It grows at 50° C. and the guanine and cytosine content (GC %) of its nucleric acid is 44%.

With reference to "Bargey's Manual of Determinative Bacteriology", 8th edition (1974), the present strain was judged to be a strain belonging to the genus Bacillus in view of the above-described principal characteristics thereof. As a result of a study through a comparison between the principal characteristics of the present strain and those of *Bacillus licheniformis, Bacillus cereus* and *Bacillus coagulans*, which are similar microorganisms, with reference to Handbook No. 427 "The genus Bacillus", various characteristics of *Bacillus licheniformis* were found to be in good conformity with those of the microorganism of this invention. However, some differences were observed in mobility and salt resistance. From the above results, the strain of this invention was judged to belong to *Bacillus licheniformis* and to be its variant strain. Therefore, the present strain was named as "*Bacillus licheniformis* B-0891".

The present strain has been deposited with the Fermentation Research Institute, Agency of Industrial Science and Technology, Ministry of International Trade and Industry, Japan under Deposition BP-952 (FERM BP-952) [date of deposit: Dec. 22, 1984].

When producing bilirubin oxidase of this invention, the above bilirubin oxidase producing microorganism is cultured in a usual manner which is employed to produce enzymes and the like. Its culture may be effected as either liquid culture or solid culture. For industrial production, it is advantageous to inoculate cells of the bilirubin oxidase producing microorganism on a culture medium suitable for use in its production and to subject them to submerged aerated-stirring culture. As the composition of the culture medium for the culture of bilirubin oxidase, may be chosen from a wide variety of culture media which are routinely used for the culture of microorganisms. Its nitrogen source may be any metabolizable nitrogen compound. For example, corn steep liquor, peptone, casein, sbybean flour, yeast extract, various meat extracts and the like may be employed. Any metabolizable carbon compound may be employed as a carbon source. For example, molasses, glucose, glycerin, sucrose, dextrin and the like may be used. Besides, various inorganic salts such as sodium chloride, potassium chloride, magnesium sulfate, potassium primary phosphate and potassium secondary phosphate may also be used as needed. The culturing temperature may be suitably adjusted within a temperature range in which the microorganism is allowed to grow and to produce bilirubin oxidase. Preferably, it is 25°–30° C. The culturing time may somewhat vary depending on conditions. It is usually 7–8 days or so. Needless to say, it is desirable to finish the culture at a suitable time point by watching the time point at which bilirubin oxidase reaches its maximum potency.

After completion of the culture, a usual enzyme-preparing method may be used to purify the enzyme from the cultured broth. Although the enzyme is found in both cells and cultured broth supernatant, the enzyme is normally obtained, from the viewpoint of the efficiency of its preparation and the like, from the supernatant obtained by removing cells from the cultured broth. It is however possible to prepare the enzyme from the cells by a usual method and to use it in combination with that obtained from the supernatant. The thus-obtained crude enzyme solution is purified by a conventional isolation and purification method which is employed for proteins, enzymes and the like, thereby obtaining bilirubin oxidase in its purified form. For example, a solution containing crude bilirubin oxidase may be subjected to a fractional precipitation method making use of an organic solvent such as acetone, methanol or ethanol or to a salting-out method employing ammonium sulfate, sodium chloride or aluminum sulfate, thereby causing the enzyme to precipitate from the solution and recovering it in a crude form.

Upon subsequent purification of the crude enzyme which may be practiced if necessary, the precipitate is dissolved in a solvent such as tris-HCl buffer. The resultant solution is then purified by suitably combining adsorption chromatography, which makes use of an ion-exchange resin such as diethylaminoethylcellulose, diethylaminoethyldextran gel or quaternary aminoethyl-dextran gel, and adsorption chromatography which employs an gel filter aid such as dextran gel or polyacrylamide gel. Thereafter, it is dried by such a technique as lyophilization to obtain bilirubin oxidase in its purified form.

The followings are physical and chemical properties of the thus-obtained bilirubin oxidase:

(I) Method for the measurement of activity:

| | |
|---|---|
| 0.2 M Tris-HCl buffer (pH 8.0, 1 mM EDTA contained) | 0.5 ml |
| Water | 0.94 ml |
| Bilirubin oxidase solution | 0.05 ml |

A reaction mixture (1.49 ml) of the above composition was placed in a small test tube. After heating it to 37° C., 0.01 ml of a 10 mM bilirubin solution was added to initiate the reaction. They were reacted at 37° C. for 10 minutes. After the reaction, 1.5 ml of 1% CPC (N-cetylpyridinium chloride) was added to terminate the reaction and the reaction mixture was subjected to the colorimetric analysis at 453 nm to determine its absorbance [S]. On the other hand, as a blank, a reaction mixture (1.44 ml) of the same type as the above-employed reaction mixture except for the exclusion of the enzyme solution was added with 0.01 ml of the bilirubin solution. The resultant mixture was incubated at 37° C. for 10 minutes precisely. Thereafter, 1.5 ml of 1% CPC and 0.05 ml of the bilirubin oxidase solution were added successively. The thus-prepared mixture was subjected to the colorimetric analysis at 453 nm to determine its absorbance [B]. The enzymatic activity is calculated in accordance with the following equation:

$$\text{Enzymatic activity (U/ml)} = \frac{([B] - [S]) \times 3.0}{60.7 \times 10 \times 0.05}$$

wherein 1 unit (U) of the enzymatic activity is defined as the amount of enzyme which oxidizes 1 $\mu$mol of bilirubin per minute under the above-described conditions.

(II) Substrate specificity

Using oxygen electrodes, specificity to various substrates was investigated based on the consumption rates of oxygen. Results are summarized in Table 2. Each of the substrates was used in an amount of 0.1 mM, while the enzyme was used in an amount of 0.005 U.

TABLE 2

| | Relative activity (%) |
|---|---|
| Bilirubin | 100 |
| Biliverdin | 0.51 |
| Pyrogallol | 92.9 |
| Catechol | 64.9 |
| Chlorophyllin | 82.5 |
| Phenol | 0.0 |
| 4-Aminoantipyrine | 0.0 |
| Hemin | 0.0 |
| Hemoglobin | 0.0 |

(III) Enzymatic reaction

The following reaction is catalyzed.

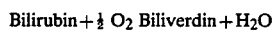

Bilirubin + ½ O$_2$ Biliverdin + H$_2$O

However, the oxidation of biliverdin into a light purple substance, which is shown by the following equation, takes place to an extremely little extent.

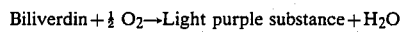

Biliverdin + ½ O$_2$ → Light purple substance + H$_2$O (IV) Thermostability

Figure 1:
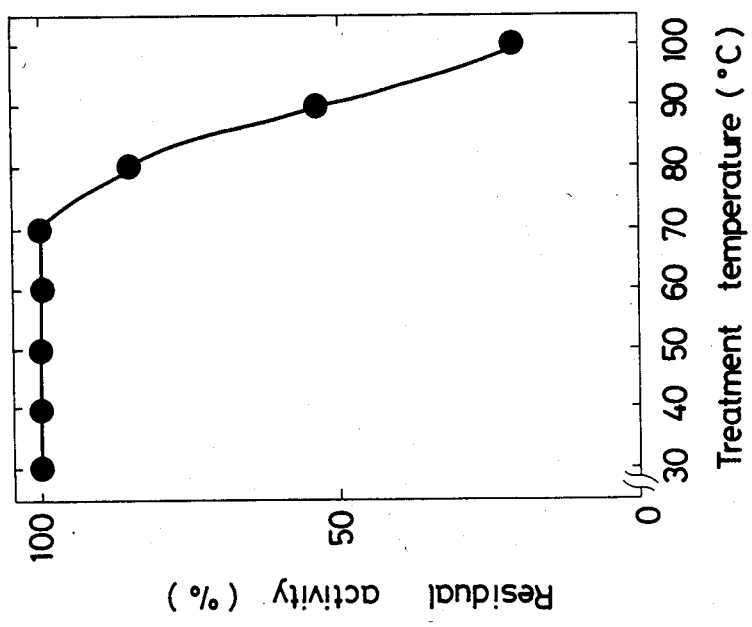
FIG. 1 shows the good thermostability of the bilirubin oxidase of this invention.
Figure 4:
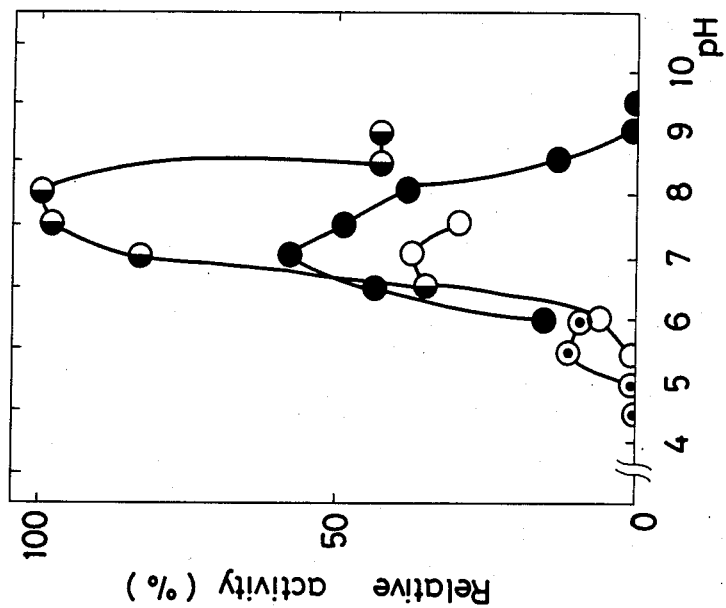
FIG. 4 shows the optimum pH of the bilirubin oxidase of this invention.

After treating portions of the enzyme for 10 minutes respectively at various temperatures ranging from 30° C. to 100° C., the portions were cooled in ice-water. Their residual activities were then measured by the enzymatic activity assay method. Results are shown in FIG. 1. The activity of the bilirubin oxidase of this invention remained stable up to about 70° C. and more than 50% of its activity remained even at 90° C.

(V) Optimum temperature

Using the reaction mixture and measurement method employed in the above assay method (I), the influence of temperature was investigated at various temperatures.

Results are shown in FIG. 2. The optimum temperature of the bilirubin oxidase of this invention was found to be around 80° C.

(VI) pH Stability

Portions of the present enzyme were incubated at 37° C. for 1 hour in buffers of various pH levels respectively. Thereafter, their activities were measured by the above-described assay method to determine the influence of pH.

Figure 3:
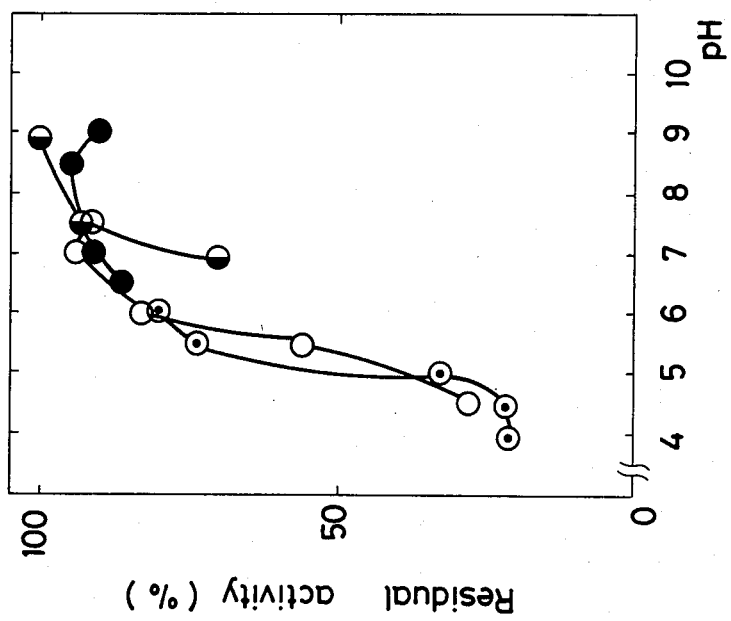
FIG. 3 depicts the good pH stability of the bilirubin oxidase of this invention.

Results are shown in FIG. 3, in which ⊚ — ⊚ , ○—○ , ●—● and ◐ — ◐ indicate acetate buffer (pH 4.0–6.0), dimethylglutaric acid-NaOH buffer (pH 7.5–9.0), phosphate buffer (pH 6.5–8.0) and tris-HCl buffer (pH 7.5–9.0) respectively. The bilirubin oxidase of this invention was found to be stable around pH 7–9.

(VII) Optimum pH

The influence of pH to the activity of the enzyme of this invention was investigated by using buffers of various pH levels as buffers in the above-described assay method.

Results are shown in FIG. 3, in which ⊚ — ⊚ , ○—○ , ●—● and ◐ — ◐ indicate acetate buffer (pH 4.0–6.0), dimethylglutaric acid-NaOH buffer (pH 7.5–9.0), phosphate buffer (pH 6.5–8.0) and tris-HCl buffer (pH 7.5–9.0) respectively. The optimum pH for the bilirubin oxidase of this invention was found to be around pH 8.

(VIII) Inhibition and activation

The bilirubin oxidase of this invention was inhibited by metal ions of $Cu^{2+}$, $Zn^{2+}$ and $Mn^{2+}$, CPC and Cation FB (trade name; product of Nippon Oils and Fats Co., Ltd.) and activated by FAD.

(IX) Molecular weight 50,000 ± 10,000 (as measured by gel filtration on "Sephacryl S-300").

(X) Isoelectric point

As a result of a measurement by the isoelectric focusing electrolysis, the isoelectric point was found to be around pH 3.35.

(XI) Km value $2.86 \times 10^{-5}$ M (at pH 8.0).

In Table 3, the enzyme of this invention is compared with conventional bilirubin oxidase samples.

TABLE 3

|  | Invention Sample | Prior Art* Sample No. 1 | Prior Art** Sample No. 2 | Prior Art*** Sample No. 3 |
| --- | --- | --- | --- | --- |
| Molecular weight | 50,000 | 44,000 | 58,000 | 52,000 |
| Isoelectric point | 3.35 | 3.98 | 6.0–6.1 | 4.1 |
| Thermostability**** | 70° C. | 60° C. | 45° C. | 37° C. |
| Optimum temperature | 80° C. | 50–60° C. | 50° C. | 40° C. |
| pH Stability | 7–9 | 5–11 | 7.5–8 | 5.0–9.7 |
| Optimum pH | 8 | 6–9 | 5.5–6 | 8 |
| Km value | $2.86 \times 10^{-5}$ M | — | — | $1.9 \times 10^{-4}$ M |

*Originated from Coprinus.
**Originated from Schizophyllum.
***Originated from Myrothecium.
****The maximum temperature having residual activity of 90% or higher in the heat treatment over 10 minutes.

As has been described above, the enzyme of this invention is different from any one of the known bilirubin oxidase samples in view of its various enzymochemical and physiochemical characteristics. Pertaining to thermostability, the residual activity after a treatment at 60° C. for 10 minutes was 90–95% even in the case of the bilirubin oxidase originated from Coprinus, which had the best thermostability among the conventional bilirubin oxidase samples, whereas the bilirubin oxidase of this invention remained stable up to 70° C. in the same 10 minute treatment and still showed residual activity as high as 50% even after treated at 90° C. for 10 minutes. Accordingly, the bilirubin oxidase of this invention is considered to be a highly thermostable enzyme. Besides, the enzyme of this invention had a very small Km value, i.e., $2.86 \times 10^{-5}$ M and its reactivity was extremely good.

Having generally described this invention, a further understanding can be obtained by reference to a certain specific example which is provided herein for purpose of illustration only and is not intended to be limiting unless otherwise specified.

EXAMPLE

*Bacillus licheniformis* B-0891 (FERM BP-952) was inoculated in a 500 ml Erlenmeyer flask which contained 100 ml of a culture medium (sterilized at 120° C. for 20 minutes; pH 7.5) containing 1.0% (W/V) of sucrose, 1.0% (W/V) of yeast extract ("Meast ®", product of Asahi Breweries, Ltd., Tokyo, Japan), 0.3% (W/V of NaCl, 0.05% (W/V) of $MgSO_4 \cdot 7H_2O$ and 0.1% (W/V) of $K_2HPO_4$, and was then cultured with shaking at 30° C. for 24 hrs to obtain a seed culture. Thereafter, the seed culture was inoculated in a jar fermenter having a capacity of 30 l and containing 20 l of a culture medium (sterilized at 120° C. for 20 minutes; pH 7.5; with 0.1% of a defoaming agent "Disfoam CB-442, trade name; product of Nippon Oils & Fats Co., Ltd." contained therein) having the same composition as the above culture medium and was cultured with aerated stirring at 30° C. and 300 rpm, for 8 days and under aeration conditions of 20 l/min. After completion of the culture, the cultured broth was centrifuged (at 5,000 rpm for 15 minutes) to obtain a supernatant (13.8 l, 200 U). The supernatant was subjected to ultrafiltration (on a module apparatus) to concentrate it to 1.96 l. The resultant concentrate was then added with chilled acetone in a volume 0.6 times the concentrate, followed by its centrifugation (at 5,000 rpm for 15 minutes) to remove insoluble matter. Thereafter, the thus-prepared concentrate was added with chilled acetone in a volume 1.6 times the concentrate so as to have a bilirubin oxidase active fraction to precipitate. The bilirubin oxidase active fraction was removed by centrifugation (at 5,000 rpm for 15 minutes) and the precipitate was dissolved in 0.2 M tris-HCl buffer to obtain an enzyme solution in a volume of 205 ml (200 U). Using a cellulose acetate tube, the enzyme solution was dialyzed overnight against 15 l of 10 mM tris-HCl buffer (pH 7.5). Thereafter, the dialyzate was adsorbed on a DEAE-Sepharose CL-6B column (5.0 × 14.5 cm) which had in advance bufferized with the above buffer. The column was then subjected to elution by density gradiation with 0–1.0 molar of potassium chloride. Enzyme active fractions eluted over the potassium chloride concentrations of 0.3–0.5 mole were recovered to collect the enzyme of this invention. Furthermore, the bilirubin oxidase active fractions were concentrated through an ultrafiltration membrane "XM-50" (trade name; product of Amicon, Corp.), followed by its development with 10 mM tris-HCl buffer (pH 7.5) on a Sephacryl S-200 column (3.6 × 80 cm). Bilirubin oxidase active fractions over developer fractions of 580–640 ml were recovered and were then lyophilized to obtain 350 mg (90.0 U) of bilirubin oxidase in its powdery form.

Having now fully described the invention, it will be apparent to one of ordinary skill in the art that many changes and modifications can be made thereto without departing from the spirit or scope of the invention as set forth herein.

What is claimed as new and is secured by Letters Patent is:

1. A bilirubin oxidase having substrate specificity to at least bilirubin and being capable of catalyzing a reaction in which biliverdin and water are formed from bilirubin and oxygen, wherein said bilirubin oxidase has the following physical and chemical properties:
    (a) a molecular weight of 50,000 ± 10,000 as measured by gel filtration on "Sepharyl S-300";
    (b) an isoelectric point at about pH 3.35;
    (c) a Km value of about $2.86 \times 10^{-5}$ M;
    (d) an optimum pH of about pH 8;
    (e) a stable pH of around pH 7 to 9;
    (f) an optimum temperature of about 80° C.; and
    (g) stability at temperatures of up to about 70° C.

2. The bilirubin oxidase of claim 1, wherein said bilirubin oxidase is obtained from *Bacillus licheniformis* B-0891 strain (FERN BP-952).

3. The bilirubin oxidase of claim 1, being capable of catalyzing a reaction between oxygen an pyrogallol, catechol and chlorophyllin.

4. The biliumbin oxidase of claim 1, said bilirubin oxidase retaining at least 50% of its acitvity after being exposed to a temperature of 90° C. for 10 minutes.

5. A process for producing a bilirubin oxidase, which comprises:

culturing a bilirubin oxidase- producing *Bacillius licheniformis* B-0891 strain (FERM BP-952); and isolating bilirubin oxidase produced in the cultured broth.

6. The process of claim 5, comprising culturing said bilirubin oxidase-producing *Bacillus licheniformis* in a submerged areated-stirring culture.

7. The process of claim 5, comprising culturing said bilirubin oxidase producing *Bacillus licheiformis* at a temperature of from 25° to 30° C. for 7 to 8 days.

8. In an assay for determining the bilirubin content of a serum sample, the improvement comprising using a bilirubin oxidase having substrate specificity to at least bilirubin and being capable of catalyzing a reaction in which biliverdin and water are formed from bilirubin and oxygen, wherein said bilirubin oxidase is thermally stable for 10 minutes at a temperature of around 70° C., wherein said bilirubin oxidase has the following physical and chemical properties:
  (a) a molecular weight of $50,000 \pm 10,000$ as measured by gel filtration on "Sephacryl S-300";
  (b) an isoelectric point at about pH=3.35;
  (c) a Km value of about $2.86 \times 10^{-5}$ M;
  (d) an optmum pH of about pH 8;
  (e) a stable pH of around pH 7 to 9; and
  (f) an optimum temperature about 80° C.

9. In a process for removing bilirubin from a serum sample to eliminate errors in the analysis of another biochemical substance in said serum sample, the improvement comprising using a bilirubin oxidase having substrate specificity to at least bilirubin and being capable of catalyzing a reaction in which biliverdin and water are formed from bilirubin and oxygen, wherein bilirubin oxidase is thermally stable for 10 minutes at a temperature of around 70° C., wherein said bilirubin oxidase has the following physical and chemical properties:
  (a) a molecular weight of $50,000 \pm 10,000$ as measured by gel filtration on "Sephacryl S-300";
  (b) an isoelectric point of about pH=3.35;
  (c) a Km value of about $2.6 \times 10^{-5}$ M;
  (d) an optimum pH of about pH 8;
  (e) a stable pH of around pH 7 to 9; and
  (f) an optimum temperature of about 80° C.

* * * * *